(12) United States Patent
Douglas

(10) Patent No.: US 7,689,368 B2
(45) Date of Patent: Mar. 30, 2010

(54) SYSTEMS AND METHODS FOR EARLY DETECTION OF MACHINE COMPONENT FAILURE

(75) Inventor: Richard David Douglas, Washington, IL (US)

(73) Assignee: Caterpillar Inc., Peoria, IL (US)

( * ) Notice: Subject to any disclaimer, the term of this patent is extended or adjusted under 35 U.S.C. 154(b) by 128 days.

(21) Appl. No.: 11/977,930

(22) Filed: Oct. 26, 2007

(65) Prior Publication Data

US 2009/0107219 A1 Apr. 30, 2009

(51) Int. Cl.
*G01N 37/00* (2006.01)
(52) U.S. Cl. .................. 702/33; 702/127; 73/61.71; 73/61.63; 73/37; 324/71.1; 340/870.28
(58) Field of Classification Search .................. 702/33, 702/127; 73/861.42, 61.71, 61.64, 61.73, 73/61.63, 37; 700/29; 422/73, 68.1; 600/445, 600/329, 453; 324/71.1, 204; 340/870.28
See application file for complete search history.

(56) References Cited

U.S. PATENT DOCUMENTS

| | | | |
|---|---|---|---|
| 4,613,815 A | 9/1986 | Christel, Jr. | |
| 5,117,675 A * | 6/1992 | Notoyama et al. | 73/37 |
| 5,563,351 A | 10/1996 | Miller | |
| 5,764,509 A | 6/1998 | Gross et al. | |
| 6,392,562 B1 * | 5/2002 | Boston et al. | 340/870.28 |
| 6,474,144 B1 * | 11/2002 | Barnes et al. | 73/61.71 |
| 6,556,939 B1 | 4/2003 | Wegerich | |
| 6,561,010 B2 * | 5/2003 | Wilson et al. | 73/54.04 |
| 6,668,039 B2 * | 12/2003 | Shepard et al. | 378/47 |
| 6,810,718 B2 * | 11/2004 | Wilson et al. | 73/54.01 |
| 6,859,517 B2 * | 2/2005 | Wilson et al. | 378/47 |
| 6,876,943 B2 | 4/2005 | Wegerich | |
| 6,936,160 B2 | 8/2005 | Moscaritolo et al. | |
| 7,082,758 B2 * | 8/2006 | Kageyama et al. | 60/445 |
| 7,233,886 B2 | 6/2007 | Wegerich et al. | |
| 7,456,960 B2 * | 11/2008 | Cerni et al. | 356/336 |
| 2001/0013247 A1 * | 8/2001 | Wilson et al. | 73/54.01 |
| 2003/0101801 A1 * | 6/2003 | Wilson et al. | 73/54.01 |

(Continued)

FOREIGN PATENT DOCUMENTS

JP 2000-241306 9/2000

OTHER PUBLICATIONS

Abstract of JP 2000-241306 in English language.

*Primary Examiner*—Carol S Tsai
(74) *Attorney, Agent, or Firm*—Finnegan, Henderson, Farabow, Garrett & Dunner

(57) ABSTRACT

A system for early detection of component failure in a hydraulic system comprises a particle detection device disposed in a fluid flow channel of a machine, the particle detection device configured to monitor a current particle count associated with fluid flowing through the fluid flow channel. The system further includes a condition monitoring system in wireless data communication with the particle detection device. The condition monitoring system is configured to receive data indicative of the current particle count and analyze historic particle count data collected by the particle detection device. The condition monitoring system is also configured to estimate a trend in the historic particle count data based on the analysis. A failure event associated with one or more components associated with the fluid flow channel is predicted if the data indicative of the current particle count deviates from the trend by a threshold amount.

20 Claims, 3 Drawing Sheets

U.S. PATENT DOCUMENTS

| | | |
|---|---|---|
| 2003/0128805 A1* | 7/2003 | Shepard et al. ............... 378/47 |
| 2004/0078171 A1 | 4/2004 | Wegerich et al. |
| 2004/0213373 A1* | 10/2004 | Wilson et al. ................ 378/42 |
| 2004/0243636 A1 | 12/2004 | Hasiewicz et al. |
| 2006/0067465 A1* | 3/2006 | Wilson ........................ 378/47 |
| 2006/0274309 A1* | 12/2006 | Cerni et al. ................. 356/338 |
| 2007/0005311 A1 | 1/2007 | Wegerich et al. |
| 2008/0087076 A1* | 4/2008 | Busch ....................... 73/61.71 |

* cited by examiner

SYSTEMS AND METHODS FOR EARLY DETECTION OF MACHINE COMPONENT FAILURE

TECHNICAL FIELD

The present disclosure relates generally to condition monitoring and telemetry systems for on-highway and off-highway machines and, more particularly, to systems and methods for early detection of machine component failure in on-highway and off-highway machines.

BACKGROUND

On-highway and off-highway machines typically comprise a plurality of components that cooperate to perform a variety of tasks. Failure of one or more components of the machine can often lead to a loss in some functionality of the machine, which may limit the performance capabilities of the machine. Some component failure events may be relatively minor and simple to detect and resolve, with no real collateral damage to other components of the machine. Other failure events, however, may be more serious, potentially damaging other components of the machine. For example, in hydraulic systems, a catastrophic pump failure may expel failure debris into the hydraulic fluid. This debris may be absorbed by one or more other components of the hydraulic system, potentially damaging these components.

While failure debris may be prevented from circulating through the entire hydraulic system through the use of one or more hydraulic filters, the buildup of debris may reduce the flow rate of the fluid. In hydraulic systems that deliver for performing tasks associated with the hydraulic system, the reduction in flow rate may prevent the requisite amount of fluid from reaching one or more critical components. Over time, these components may overheat, increasing the likelihood for premature wear and, eventually, failure of these components.

One method for identifying buildup of debris in hydraulic system involves the use of a pressure differential switch that monitors the input and output pressure of the filter. If the pressure differential exceeds a threshold value, the switch is triggered and a warning signal is generated notifying the machine operator that the filter may be clogged with debris, which may be indicative of a catastrophic failure of one or more components associated with the hydraulic system.

One problem with threshold-based failure detection circuits is that, because component failure often manifests itself very quickly, the pressure differential may not be large enough to trigger the alarm until after the failure event has occurred. Such late detection of failure events may potentially cause damage to other components in the fluid channel, as contaminate particles that may have been expelled by the failed component may cause damage to components located between the failed component and the fluid filter. These particles may be difficult to remove once introduced to the system, and in addition to causing catastrophic component failure to one or more components in the short-term, may lead to long-term contingent component wear as these residual particles may remain in the system indefinitely.

Furthermore, late detection of failure events for certain "critical" components such as, for example, a hydraulic pump used to drive the tracks of a machine, may dramatically decrease worksite productivity. For example, if the failure event immobilizes or otherwise disables the machine, performance of tasks that depend upon the operation of the machine may be delayed. In addition, if the machine breaks down while operating in the worksite, the machine may present an obstacle to other machines. Thus, in order to limit the effects of catastrophic component failure and/or contingent component failure on the operations of a machine and worksite, a system for early detection of machine component failure may be required.

At least one system has been developed for predicting a remaining lifespan of a hydraulic pump. For example, U.S. Pat. No. 7,082,758 ("the '758 patent) to Kageyama et al. describes a system for monitoring long-term and short-term trends associated with pressure differential data measured across a hydraulic filter. The system may predict a pump failure or estimate a pump lifespan based on the degree of deviation between the long-term trend data and the short-term trend data.

Although the system of '758 patent may be effective in predicting component failure in certain situations, the system of the '758 patent may have several disadvantages. For example, differential pressure across the pump filter will typically only begin increasing after the filter chamber has filled, which may not occur until after significant failure contaminates have already been introduced into the fluid. Consequently, by the time the system of the '758 patent detects an upward trend in the differential pressure across the filter, one or more components may have already sustained significant damage.

The presently disclosed systems and methods for early detection of machine component failure are directed toward overcoming one or more of the problems set forth above.

SUMMARY

In accordance with one aspect, the present disclosure is directed toward a method for early detection of component failure in a hydraulic system. The method may comprise implanting a particle detection device in a fluid flow channel associated with a machine, the particle detection device configured to monitor a current particle count associated with fluid flowing through the fluid flow channel. The method may also include receiving, in a condition monitoring system, data indicative of the current particle count and analyzing historic particle count data collected by the particle detection device. A trend in the historic particle count data may be estimated based on the analysis. A failure event associated with one or more components associated with the fluid flow channel may be detected if the data indicative of the current particle count deviates from the trend by a threshold amount.

According to another aspect, the present disclosure is directed toward a system for early detection of component failure in a hydraulic system. The system may comprise a particle detection device disposed in a fluid flow channel of a machine. The particle detection device may be configured to monitor a current particle count associated with fluid flowing through the fluid flow channel. The system may further include a condition monitoring system in wireless data communication with the particle detection device. The condition monitoring system may be configured to receive data indicative of the current particle count and analyze historic particle count data collected by the particle detection device. The condition monitoring system may also be configured to estimate a trend in the historic particle count data based on the analysis. A failure event associated with one or more components associated with the fluid flow channel may be predicted if the data indicative of the current particle count deviates from the trend by a threshold amount.

In accordance with another aspect, the present disclosure is directed toward a machine comprising a fluid flow channel for delivering fluid to one or more components associated with the machine. The machine may include a particle detection device disposed in the fluid flow channel, the particle detection device configured to monitor a current particle count associated with fluid flowing through the fluid flow channel. The machine may also include a data collector disposed on-board the machine and communicatively coupled to the particle detection device, the data collector being configured to receive the particle count data from the particle detection device. The machine may further include a condition monitoring system in wireless data communication with the particle detection device. The condition monitoring system may be configured to analyze historic particle count data collected by the particle detection device and estimate a trend in the historic particle count data based on the analysis. The condition monitoring system may also be configured to predict a failure event associated with one or more components associated with the fluid flow channel if the data indicative of the current particle count deviates from the trend by a threshold amount. The condition monitoring system may further be configured to generate a failure event notification associated with a predicted failure event.

DETAILED DESCRIPTION

Figure 1:
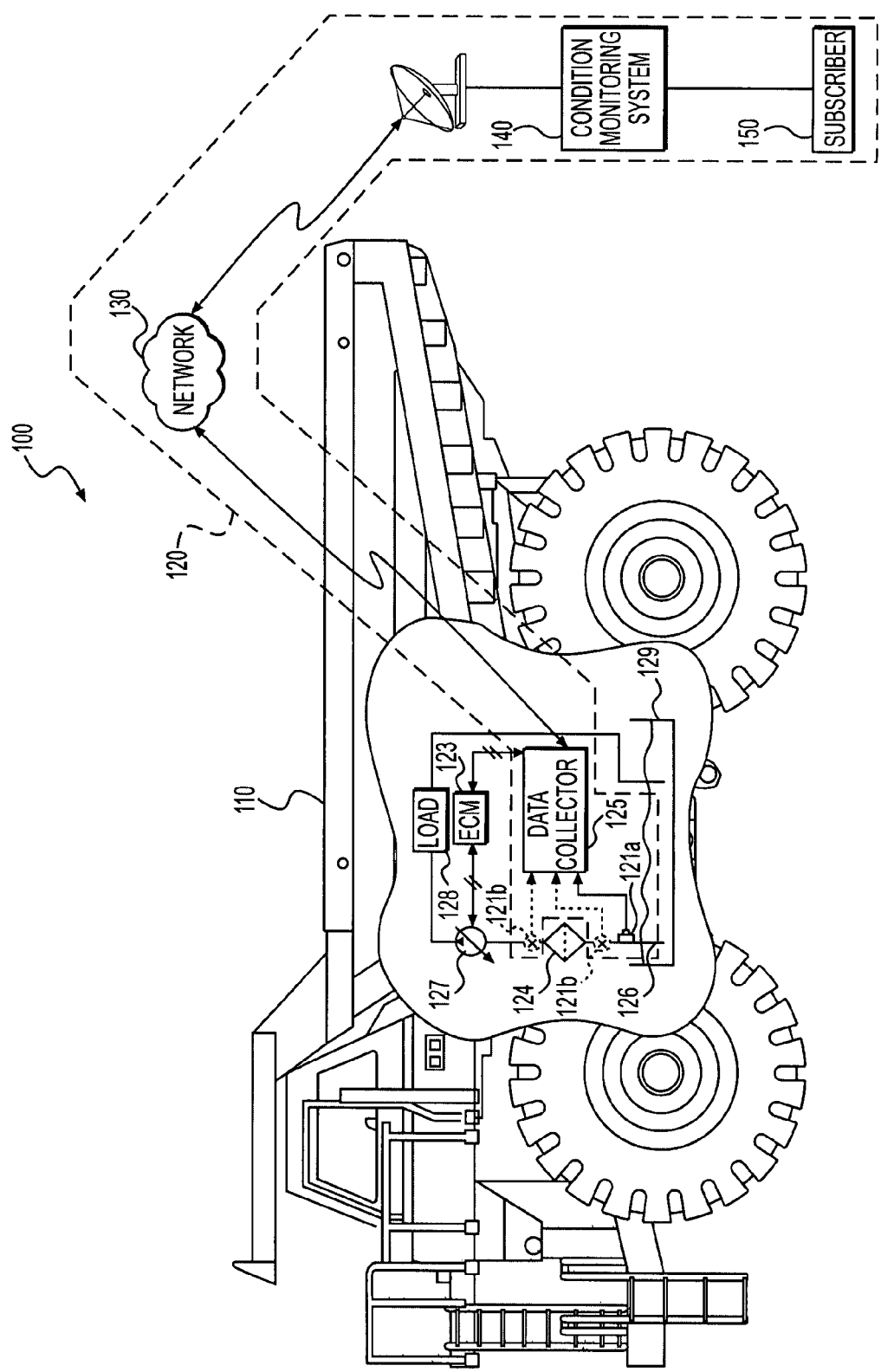
FIG. 1 illustrates an exemplary project environment consistent with the disclosed embodiments.

FIG. 1 illustrates an exemplary project environment 100 consistent with certain disclosed embodiments. Project environment 100 may include one or more components that perform individual tasks that contribute to a machine environment task, such as mining, construction, transportation, agriculture, manufacturing, or any other type of task associated with other types of industries. For example, project environment 100 may include one or more machines 110 coupled to a condition monitoring system 140 via one or more communication networks 130. The project environment 100 may be configured to monitor, collect, control, and/or filter information associated with an operation of one or more machines 110 and distribute the information to one or more back-end systems, such as condition monitoring system 140 and/or subscribers 150. It is contemplated that additional and/or different components than those listed above may be included in project environment 100.

Machine 110 may be a fixed or mobile machine configured to perform an operation associated with project environment 100. Thus, machine, as the term is used herein, refers to a fixed or mobile machine that performs some type of operation associated with a particular industry, such as mining, construction, farming, etc. and operates between or within project environments (e.g., construction site, mine site, power plants, etc.) Furthermore, machine 110 may be used to refer to any remote asset operating within or associated with project environment 100. A non-limiting example of a fixed machine includes an engine system operating in a plant, a material conveyer, or off-shore environment (e.g., off-shore drilling platform). Non-limiting examples of mobile machines include commercial machines, such as trucks, cranes, earth moving vehicles, mining vehicles, backhoes, material handling equipment, farming equipment, marine vessels, aircraft, and any type of movable machine that operates in a work environment. A machine may be driven by a combustion engine or an electric motor. The types of machines listed above are exemplary and not intended to be limiting. It is contemplated that project environment 100 may implement any type of machine. Accordingly, although FIG. 1 illustrates machine 110 as a mobile earth-moving machine, machine 110 may be any type of machine operable to perform a particular function within project environment 100.

Machine 110 may include on-board data collection and communication equipment to monitor, collect, and/or distribute information associated with one or more components of machines 110. According to one embodiment, on-board data collection and communication equipment may include a system 120 for early detection of failure of one or more components associated with machine 110. It is contemplated that machine 110 may include additional on-board data collection and communication equipment. For example, machine 110 may include data monitoring equipment (e.g., sensors, control modules, data collectors, etc.) for monitoring health, productivity, status, and/or performance associated with machine 110.

System 120 may be configured to monitor one or more parameters associated with a fluid system of machine 110. For example, system 120 may be implemented as part of a hydraulic system for generating and delivering hydraulic fluid to one or more hydraulically-actuated devices that control the movement of an implement or tool associated with machine 110. Alternatively or additionally, system 120 may be implemented as part of a hydraulic transmission system that uses a pump/motor to operate the drive system for controlling the traction system of machine 110.

Machine fluid systems may typically include a fluid channel 126 that draws fluid from a reservoir 129. Fluid channel 126 may deliver the fluid through a filtration device 124, which collects and removes particulate matter from the fluid. Fluid channel 126 may then deliver the fluid to a pump 127, which compresses the fluid and facilitates circulation of the fluid within fluid channel 126 for eventual deliver to a load 128.

Fluid channel 126 may include any type of medium that may be configured to contain and direct the flow of fluid. For example, fluid channel 126 may include metallic, semi-metallic, alloy, rubber, polymer, and/or plastic pipes. Fluid channel 126 may be used to connect a fluid source, such as contained in reservoir 129, to one or more components that may operate on or otherwise utilize the fluid.

Reservoir 129 may include any type of tank for storing excess fluid that is not contained in fluid channel 126 or any components associated therewith. For example, reservoir 129 may include a storage tank adapted to store hydraulic fluid or other suitable fluid, or any other type of fluid for circulation through fluid channel 126.

Filtration device 124 may include any device for filtering, collecting, and storing contaminates, impurities, or other particulate matter from fluid flowing through fluid channel 126. For example, filtration device 124 may include an oil filter, fuel filter, or any other type of filter suitable for removing contaminates from a fluid.

Pump 127 may be configured to produce a flow of pressurized fluid and may include a variable displacement pump, a fixed displacement pump, a variable flow pump, or any other device adapted to pressurize a fluid. Pump 127 may be drivably connected to power source (not shown) by, for example, a countershaft (not shown), a belt (not shown), an electrical circuit (not shown), or in any other suitable manner. Pump 127 may be dedicated to supplying pressurized fluid to transmission, one or more hydraulic systems or components (e.g., work implements, etc.), an engine system, or other component associated with fluid channel 126.

Load 128 may be fluidly coupled to pump 127 and may embody any system that uses fluid pressurized by pump 127 to perform a task. For example, load 128 may include an implement coupled to fluid channel 126 of a hydraulic system. The implement may be configured to perform a task in response the receipt of pressurized fluid from pump 127. Excess fluid circulating through load 128 may be returned to reservoir 129 via fluid channel 126.

Machine fluid system may also include one or more devices for controlling the operation of one or more components associated with the fluid system. For example, machine fluid system may include an electronic control module 123 configured to control the operation of pump 127, one or more valves (not shown), and/or load 128. According to one embodiment, electronic control module 123 may be configured to provide one or more control signals for operating the pump in response to an operator instruction to move an implement associated with machine 110.

System 120 may include one or more components configured to monitor parameters associated with the fluid system and predict, based on the monitored parameters, failure of one or more components associated with the fluid system. System 120 may include, for example, one or more monitoring devices 121, such as a particle detection device 121*a* and one or more pressure sensors 121*b*; a data collection device 125; a communication network 130; a condition monitoring system 140; and one or more subscribers 150. It is contemplated that system 120 may include additional and/or different components than those listed above.

Monitoring devices 121 may include any device for collecting performance data associated with one or more machines 110. For example, monitoring devices 121 may include one or more sensors for measuring an operational parameter such as engine and/or machine speed and/or location; fluid pressure, flow rate, temperature, contamination level, and or viscosity of a fluid; electric current and/or voltage levels; fluid (i.e., fuel, oil, etc.) consumption rates; loading levels (i.e., payload value, percent of maximum payload limit, payload history, payload distribution, etc.); transmission output ratio, slip, etc.; haul grade and traction data; drive axle torque; intervals between scheduled or performed maintenance and/or repair operations; and any other operational parameter of machines 110.

Particle detection device 121*a* may include any device configured to monitor and measure particle count data associated with a fluid flowing through fluid channel. Particle count data, as the term is used herein may include any data indicative of particles present in a fluid. For example, particle count data may include a number and size of particle present in a fluid flowing through fluid chamber 126, the speed of the particles within the channel, the flow rate of fluid traveling through the fluid channel 126, or any other data that may be determined or derived from particles present in fluid flowing through fluid channel 126. According to one exemplary embodiment, particle count data may include the International Organization for Standardization (ISO) 4406 method for the level of contamination by solid particles.

According to one exemplary embodiment, particle detection device 121*a* may embody a laser diode particle detection module, such as, for example, the Parker Hannifin ICountPD and/or the Hydac CS1000 particle detector. Alternatively or additionally, particle detection device 121*a* may include any optical device suitable for detecting small particles in a fluid. For example, particle detection device 121*a* may include a light source for directing light through a chamber of known dimensions onto a photo detection device coupled to optical detection electronics. Light generated by the light source penetrates the fluid and, if absorbed or deflected by one or more particles, prevents light from intercepting the photo detector. Optical detection electronics analyze the image or data captured by the photo detector to determine, among other things, the number and size of particulate matter present in the fluid. In addition to the number and size of particles, particle detection device 121*a* may be configured to determine a flow rate of the fluid (based on the speed of the particles traveling through a chamber with known volumetric dimensions) and/or the speed of the traveling particles.

As an alternative or in addition to particle detection device 121*a*, system 120 may include one or more pressure sensors 121*b*. Pressure sensors 121*b* may include any device configured to monitor a pressure of fluid flowing through fluid channel 126. As illustrated in FIG. 1, pressure sensors 121*b* may be disposed at input and output ports of filtration device 124. Consequently, a pressure sensor disposed at the input port of filtration device 124 may monitor the pressure of fluid at the input of filtration device 124, while a pressure sensor disposed at the output port of filtration device 124 may monitor the pressure of fluid at the output of filtration device 124. A pressure differential corresponding with filtration device 124 may be determined as the difference between the output pressure and the input pressure across the filter.

Data collector 125 may be configured to receive, collect, package, and/or distribute data collected by monitoring devices 121. For example, data collector 125 may receive particle count data from particle detection device 121*a* and pressure data from one or more of pressure sensors 121*b*. Data collector 125 may package this data and transmit the received data to condition monitoring system 140 via communication network 130. Alternatively or additionally, data collector 125 may store the received data in memory for a predetermined time period, for later transmission to condition monitoring system 140. For example, should a communication channel between the machine and condition monitoring system 140 (e.g. communication network 130 or one or more communication devices associated with data collector 125 and/or condition monitoring system 140) become temporarily unavailable, the collected data may be stored in memory for subsequent retrieval and transmission when the communication channel has been restored.

Communication network 130 may include any network that provides two-way communication between machine 110 and an off-board system (e.g., condition monitoring system 140). For example, communication network 130 may communicatively couple machine 110 to condition monitoring system 140 across a wireless networking platform such as, for example, a satellite communication system, a cellular communication system, or any other platform for communicating data with one or more geographically dispersed assets (e.g., Bluetooth, microwave, point-to-point wireless, point-to-multipoint wireless, multipoint-to-multipoint wireless.) Although communication network 130 is illustrated as a satellite-based wireless communication network it is contemplated that communication network 130 may also include or embody any suitable wireless and/or wire-line networks such as, for example, Ethernet, fiber optic, waveguide, or any other type of wired communication network. It is also contemplated that communication network may support additional communication media or communication methods such as smartcard technology, manual data transport methods (sneakernet), or any suitable means for transporting data between machine 110 and off-board systems.

Communication network 130 may also include any necessary infrastructure to support message routing and network operations. For example, communication network 130 may include various hardware and software support systems and equipment that facilitates operations of one or more communication services.

Condition monitoring system 140 may be configured to receive, store, analyze, and record particle count and/or pressure data associated with system 120 of machine 110. For example, condition monitoring system 140 may detect one or more machines 110 associated with project environment 100. Condition monitoring system 140 may transmit a data request to one or more data collectors 125 associated with machines 110. Condition monitoring system 140 may receive data from data collectors 125 in response to the request. Alternatively or additionally, condition monitoring system 140 may be configured to automatically receive particle count and/or pressure data from data collector 125. For example, data collector 125 may be configured to automatically locate communication network 130 and transmit data to condition monitoring system 140 upon detection of communication network 130.

According to one embodiment, condition monitoring system 140 may receive particle count and/or pressure data associated with fluid channel 126 of machine 110 and store the data in memory for future analysis. For example, condition monitoring system 140 may establish a database of historic particle count and/or pressure data, sort the particle count and/or pressure data in chronological order based on when the data was monitored, and store particle count and/or pressure data in the database, for future analysis.

Condition monitoring system 140 may be any computing system configured to receive, transmit, analyze, and distribute data collected by system 120, including particle count data and data associated with other monitoring systems of one or more machines 110. As explained, condition monitoring system 140 may be communicatively coupled to one or more machines 110 via communication network 130. According to one embodiment, condition monitoring system 140 may embody a centralized server and/or database adapted to collect and disseminate particle count data and/or pressure data collected by particle detection device 121a and/or pressure sensor 121b. Once collected, condition monitoring system 140 may categorize and/or filter the data according to data type, priority, etc.

Figure 2:
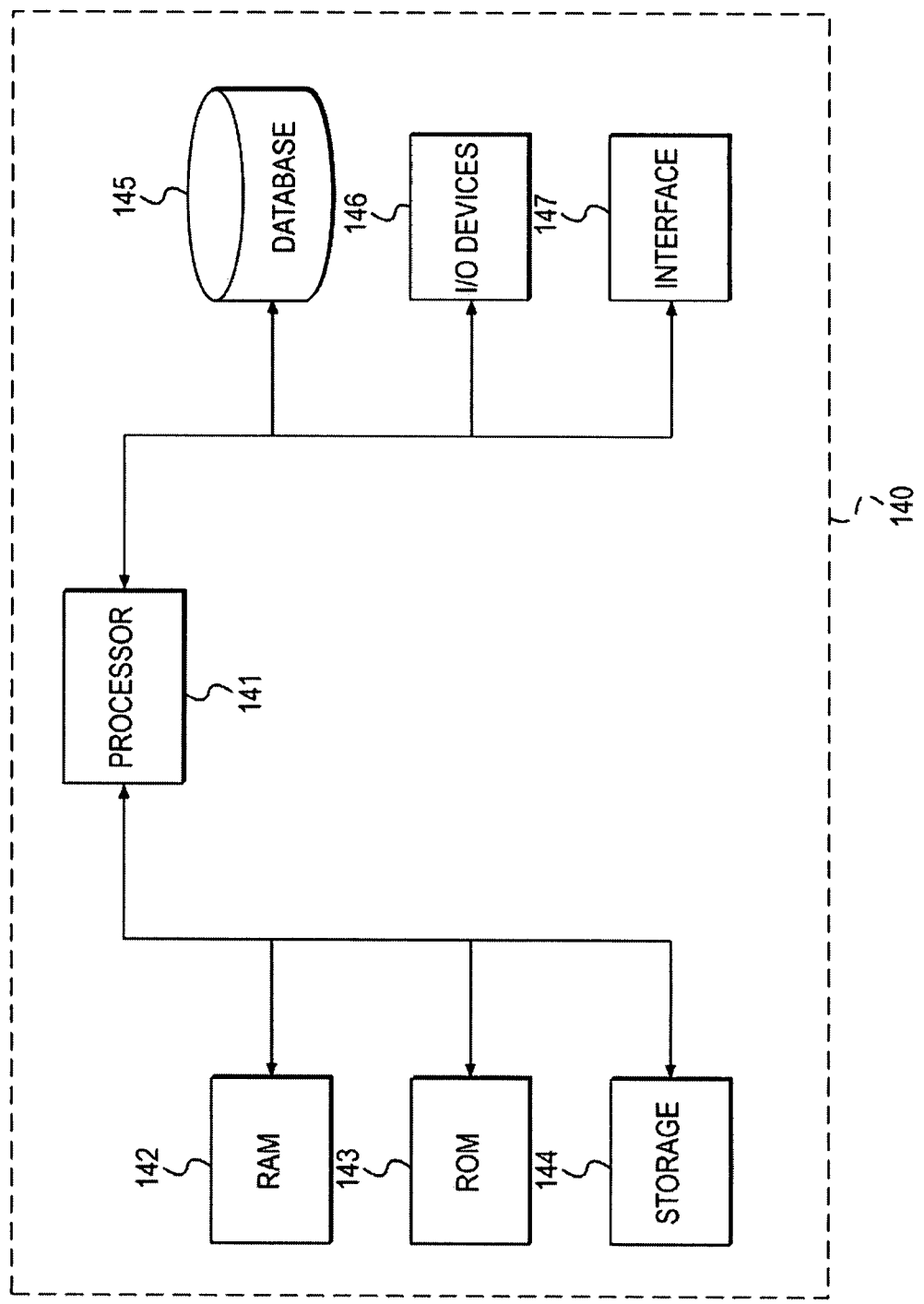
FIG. 2 illustrates an exemplary condition monitoring system on which methods and features consistent with the disclosed embodiments may be performed.

Condition monitoring system 140 may include any type of processor-based system on which processes and methods consistent with the disclosed embodiments may be implemented. For example, as illustrated in FIG. 2, condition monitoring system 140 may include one or more hardware and/or software components configured to execute software programs, such as software for monitoring and analyzing data associated with one or more machines 110. For example, condition monitoring system 140 may include one or more hardware components such as, for example, processor 141, a random access memory (RAM) module 142, a read-only memory (ROM) module 143, a storage system 144, a database 145, one or more input/output (I/O) devices 146, and an interface 147. Alternatively and/or additionally, condition monitoring system 140 may include one or more software components such as, for example, a computer-readable medium including computer-executable instructions for performing methods consistent with certain disclosed embodiments. It is contemplated that one or more of the hardware components listed above may be implemented using software. For example, storage 144 may include a software partition associated with one or more other hardware components of condition monitoring system 140. Condition monitoring system 140 may include additional, fewer, and/or different components than those listed above. It is understood that the components listed above are exemplary only and not intended to be limiting.

Processor 141 may include one or more processors, each configured to execute instructions and process data to perform one or more functions associated with condition monitoring system 140. As illustrated in FIG. 2, processor 141 may be communicatively coupled to RAM 142, ROM 143, storage 144, database 145, I/O devices 146, and interface 147. Processor 141 may be configured to execute sequences of computer program instructions to perform various processes, which will be described in detail below. The computer program instructions may be loaded into RAM for execution by processor 141.

RAM 142 and ROM 143 may each include one or more devices for storing information associated with an operation of condition monitoring system 140 and/or processor 141. For example, ROM 143 may include a memory device configured to access and store information associated with condition monitoring system 140, including information for identifying, initializing, and monitoring the operation of one or more components and subsystems of condition monitoring system 140. RAM 142 may include a memory device for storing data associated with one or more operations of processor 141. For example, ROM 143 may load instructions into RAM 142 for execution by processor 141.

Storage 144 may include any type of mass storage device configured to store information that processor 141 may need to perform processes consistent with the disclosed embodiments. For example, storage 144 may include one or more magnetic and/or optical disk devices, such as hard drives, CD-ROMs, DVD-ROMs, or any other type of mass media device.

Database 145 may include one or more software and/or hardware components that cooperate to store, organize, sort, filter, and/or arrange data used by condition monitoring system 140 and/or processor 141. For example, database 145 may include historical data such as, historic (e.g. previously detected) particle count data and/or pressure data associated with fluid channel 126. Trends may be recorded and analyzed to determine whether current particle count data and/or pressure data is consistent with "normal" particle count and/or pressure trends. It is contemplated that database 145 may store additional and/or different information than that listed above.

I/O devices 146 may include one or more components configured to communicate information with a user associated with condition monitoring system 140. For example, I/O devices may include a console with an integrated keyboard and mouse to allow a user to input parameters associated with condition monitoring system 140. I/O devices 146 may also include a display including a graphical user interface (GUI) for outputting information on a monitor. I/O devices 146 may also include peripheral devices such as, for example, a printer for printing information associated with condition monitoring system 140, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 147 may include one or more components configured to transmit and receive data via a communication network, such as the Internet, a local area network, a workstation peer-to-peer network, a direct link network, a wireless network, or any other suitable communication platform. For example, interface 147 may include one or more modulators, demodulators, multiplexers, demultiplexers, network communication devices, wireless devices, antennas, modems, and any other type of device configured to enable data communication via a communication network.

Condition monitoring system 140 may include one or more software applications for detecting a future failure of a component associated with the machine fluid system and notifying one or more subscribers 150 (e.g., repair personnel, project managers, dispatchers, etc.). For example, software application associated with condition monitoring system 140 may be configured to analyze the historic particle count and pressure data to estimate a trend in the historic data. Condition monitoring system 140 may compare current (e.g., real-time) particle count data with the historic trend data. If the current particle count data exceeds the historic particle count trend by a predetermined acceptable amount, condition monitoring system 140 may trigger a failure event detection alarm and/or generate an event notification for distribution to one or more subscribers 150.

Subscriber 150 may include a computer system or mobile data device that is configured to receive data from condition monitoring system 140 in a manner consistent with the disclosed embodiments. For example, subscriber 150 may include one or more computer terminals operated by respective users. Alternatively and/or additionally, subscriber 150 may include personal data assistant systems (PDA), wireless communication devices (e.g., pagers, phones, etc.), notebook computers, diagnostic computer systems, data analyzers, or any other such computing devices configured to receive and process information. In one embodiment, subscriber 150 may be associated with one or more sections of a business entity associated with managing a remote project site within project environment 100. For instance, subscriber 150 may be associated with a particular division of a business entity associated with project environment 100, such as a project management division, an operations division, a maintenance and/or repair division, a procurement division, a human resource division, and/or any other business entity that may be associated with project environment 100.

In another embodiment, subscriber 150 may be associated with a business entity that is affiliated with one or more sets of machines 110. For example, subscriber 150 may be associated with a site-manager that controls the operation and productivity of the first set of machines 110. Alternatively and/or additionally, different project entities may be associated with different business entities and/or machines 110. Accordingly, the above descriptions are exemplary and not intended to be limiting. The disclosed embodiments contemplate any correlation (or none at all) between one or more business entities, and/or sections thereof, and the components of project environment 100.

Subscriber 150 may be associated with a business entity affiliated with project environment 100 and may be configured to communicate with condition monitoring system 140. In one embodiment, subscriber 150 may transmit and receive operation data to and from condition monitoring system 140 associated with one or more machines 110 operating within project environment 100. For example, subscriber 150 may be an on-site maintenance and repair division that receives component failure alerts (and/or particle count or pressure data associated therewith) associated with one or more machines 110 from condition monitoring system 140.

Subscriber 150 may also include portable communication devices associated with one or more personnel affiliated with project environment 100. For example, subscriber 150 may include a wireless pager or cell phone associated with a project manager, machine operator, dispatcher, repair technician, shift scheduler, or machine owner. As such, subscriber 150 may receive failure event warnings and alerts from condition monitoring system 140 and schedule the machine for inspection and/or repair before the predicted failure event occurs.

Figure 3:
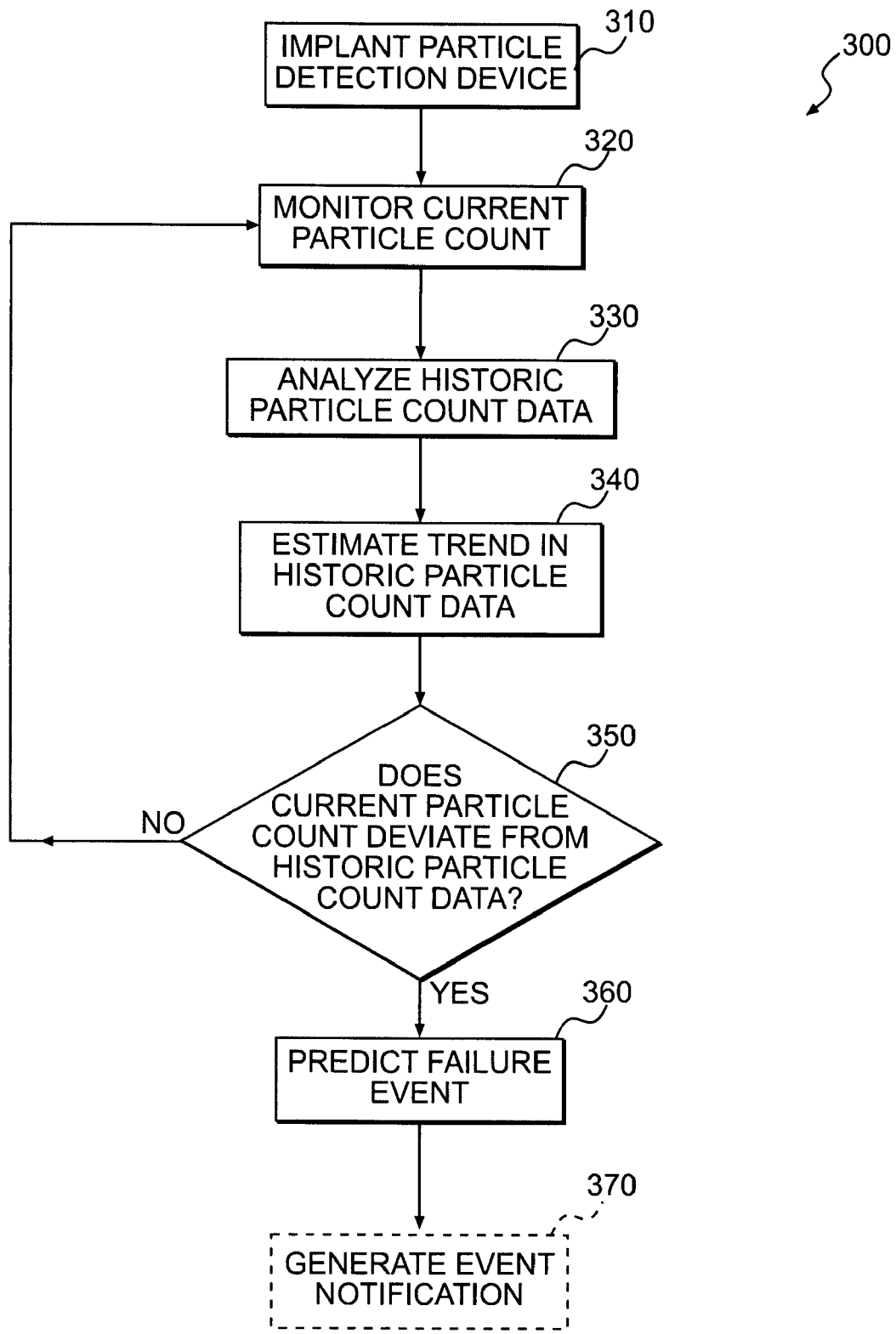
FIG. 3 provides a flowchart depicting an exemplary method for early detection of machine component failure consistent with the disclosed embodiments.

Processes and methods consistent with the disclosed embodiments provide a system for early detection of component failure associated with one or more components within a fluid flow path. More specifically, the system described herein provides a system for monitoring the trend of particle count data of fluid flowing in fluid channel 126. If current data deviates from the monitored trend by a threshold amount, a potential future failure event may be identified and the machine may be flagged for investigation, testing, and/or repair. As an alternative or additional (i.e., redundant) embodiment, the system described herein may monitor the pressure at one or more locations along fluid channel 126 and identify a trend in the pressure data. If current pressure data deviates from the pressure trend, indicating a potential buildup of contaminates and debris associated with a component failure, the system may notify a subscriber to report the potential problem. FIG. 3 provides a flowchart 300 depicting an exemplary method for early detection of machine component failure that may be performed by system 120 and/or software associated therewith.

As illustrated in FIG. 3, the method may include implanting particle detection device 121*a* within one or more machines 110 (Step 310). Specifically, particle detection device 121*a* may be disposed within fluid channel 126 of machine 110. According to one exemplary embodiment, particle detection device 121*a* may be disposed between reservoir 129 and filtration device 124 to determine, among other things, the number and size of particles entering fluid channel 126. Alternatively or additionally, particle detection device 121*a* may be disposed at any location along fluid channel 126 or at multiple locations along the channel to monitor contaminates within fluid channel 126.

Once particle detection device 121*a* has been implanted within fluid channel 126, particle count data associated with fluid channel 126 may be collected by particle detection device 121*a* (Step 320). The particle count data may be delivered to on-board data collector 125, which may subsequently upload the particle count data to an off-board back-end system, such as condition monitoring system 140. Condition monitoring system 140 may store the particle count data in database 145 as historic particle count data (e.g., particle count data previously collected by particle detection device 121*a*).

Condition monitoring system 140 may analyze historic particle count data stored in database (Step 330) and estimate a trend in historic particle count data based on the analysis (Step 340). For example, condition monitoring system 140 may determine that the number of particles present in fluid flowing in fluid channel 126 increases at a rate of 1¼%-1¾% per 10 hours of engine operation. Condition monitoring system 140 may extrapolate this data to estimate or predict certain future events. For instance, condition monitoring system 140 may predict when the number of particles present in the fluid will exceed a threshold limit and may schedule maintenance to replenish fluid and/or replace filtration device 124.

Condition monitoring system 140 may also use this data to estimate the remaining lifespan associated with certain components associated with fluid channel 126. For example, if historical trend data associated with a hydraulic system is rising at a faster rate than normal, indicating accelerated wear in one or more components (e.g., pump, gaskets, seals, etc. associated with the hydraulic system), condition monitoring system 140 may estimate the remaining lifespan of the hydraulic system and/or components associated therewith. Accordingly, condition monitoring system 140 may provide a notification to one or more subscribers 150, indicating the system maintenance and/or testing may be required.

Condition monitoring system 140 may also be configured to utilize the particle count data to schedule routine maintenance associated with machine 110. For example, because some machines may be operated in harsher and/or more rigorous environments, each machine may require different maintenance schedules for hydraulic and/or other fluid systems. More particularly, engine and/or transmission lubrication and/or cooling systems associated with machines operating in harsh environments may require more frequent maintenance to counteract the increase of particulate matter caused by normal wear and tear than machines operating under less severe conditions. Accordingly, rather than prescribing periodic maintenance at set intervals, condition monitoring system 140 may be adapted to determine when wear debris has reached a level that requires system maintenance.

While nominal increases in particle count trends is indicative of normal "wear-and-tear", dramatic deviations from these trends may be indicative of a material failure of one or more components in the system. Accordingly, as condition monitoring system 140 receives current ("real-time" or near-"real-time") particle count data from machines 110, condition monitoring system 140 may compare the current data with the historic particle count trend (Step 350). If the current particle count data does not deviate from the historic part count trend by a threshold amount (Step 350: No), condition monitoring system 140 may continue monitoring the current particle count data.

The threshold level for characterizing deviations in current particle count data with respect to historic particle count data may be predetermined based, for example, on empirical test data gathered during failure test analysis associated with components of the fluid system. Alternatively, the threshold level may be established by estimating the increase in particulate expulsion associated with certain "minor" failure events that may occur prior to complete component failure. For example, pump impeller bearings may begin to break down some time before total failure of the pump. Consequently, when the impeller bearings being to deteriorate particulate debris may be expelled into fluid channel 126. As the pump impeller condition gradually declines, additional material may be introduced into the fluid. These initial "warning signs" may be observed as uncharacteristic increases in particle count in additional to the normal "wear-and-tear" particle count data. Thus, the threshold level for an acceptable increase in historic particle count data may be established as a predetermined percentage above the historical increase. Accordingly, if the historical trend indicates that, for every 10 hours of engine operation, particle count data has increased 1½%-2½%, the threshold for characterizing a deviation in current data from historical trend data may be established as, for example, 4%.

It is contemplated that additional and/or different methods may be used for determining an acceptable threshold for identifying failure event based on particle count data. For example, if, during monitoring of a machine during a catastrophic failure event, the particle count data increased by 10% over the historical trend, the threshold level may be set as some level less than 10%. Those skilled in the art will recognize that the lower this level is set, the earlier that a failure event prediction is made, which may also increase the number of false component failure predictions.

If the current particle count data deviates from the historic particle count trend by the threshold amount (Step 350: Yes), condition monitoring system 140 may predict a component failure event (Step 360). Because components often fail very quickly from the onset of certain failure symptoms, condition monitoring system 140 may be configured to immediately generate an event notification (Step 370). This event notification may include an audible and/or visual alarm within the cab of the machine, advising the driver of a potential component failure condition.

In addition to generating an on-board machine alarm, condition monitoring system 140 may also be configured to generate an electronic message, such as a text message, e-mail message, page, short-message-service (SMS) message, automated voice message, a voicemail message, or any other suitable electronic message. Condition monitoring system 140 may transmit this message to one or more subscribers 150. As a result, subscribers 150 may be able to take appropriate action to reduce the impact of a component failure on project environment 100. For example, a project manager or dispatcher may schedule immediate maintenance with a repair facility and schedule a replacement rental machine to prevent a lapse in productivity during the repair(s).

Optionally, upon predicting a catastrophic failure associated with the machine, condition monitoring system 140 may generate a control signal to shut down the machine before the occurrence of the failure event. This may be particularly advantageous in fluid system where failure of one component may result in significant collateral damage to the machine or one or more critical components associated therewith. For example, if condition monitoring system 140 predicts a component failure associated with the fluid cooling system for an engine, condition monitoring system 140 may generate a command signal to shut down the engine to prevent overheating of the engine and damage associated therewith.

INDUSTRIAL APPLICABILITY

Systems and methods consistent with the disclosed embodiments provide a solution for early detection of failure of components associated with machine fluid systems. Machines that employ the presently disclosed systems and associated methods may be configured to detect and monitor the number and size of particles present in fluid flowing through a fluid channel. The systems and methods described herein may also detect, based on a comparison between current particle count data and historic particle count data, a future failure of one or more components within the fluid channel. As a result, work environments that implement the presently disclosed system for early detection of machine component failure may enable project managers, machine operators, and equipment owners to preemptively identify and repair damaged components before catastrophic component failure that may disable the machine and have a significant impact on the productivity of the work environment.

Although the disclosed embodiments are described and illustrated as being associated with fluid systems for heavy machinery, they may be implemented in any mobile or stationary machine comprising at least one fluid delivery system. Specifically, the presently disclosed systems and methods for early detection of machine component failure may be used in any machine or equipment system where it may be advantageous to monitor the amount of debris in a fluid, particularly in systems where circulation of debris may potentially damage components of the machine or restrict the flow of fluid necessary to ensure proper operation of the machine. Furthermore, the presently disclosed systems and associated methods may be integrated with a connected worksite environment that monitors, analyzes, and manages operations of a plurality of machines to ensure efficient operation of the worksite.

The presently disclosed systems and methods for early detection of machine component failure may have several advantages. For example, the presently disclosed system employs a particle detection device that directly monitors the number and size of particles present in the fluid, which directly detects the presence of failure debris indicative of imminent failure of a component. In contrast, conventional systems use indirect methods for detecting failure debris (e.g., by monitoring pressure drop across a fluid filter). However, such indirect methods may not immediately respond to increases in failure debris (e.g., until the fluid filter becomes clogged), potentially delaying the detection of a failure condition, which may result in further damage to the machine.

It will be apparent to those skilled in the art that various modifications and variations can be made to the disclosed systems and methods for early detection of machine component failure without departing from the scope of the disclosure. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents.

What is claimed is:

1. A method for early detection of component failure in a hydraulic system comprising:
   monitoring, by a particle detection device implanted in a fluid flow channel associated with a machine, a current particle count associated with fluid flowing through the fluid flow channel;
   receiving, in a condition monitoring system, data indicative of the current particle count;
   analyzing, in the condition monitoring system, historic particle count data collected by the particle detection device;
   estimating, in the condition monitoring system, a trend in the historic particle count data based on the analysis; and
   updating, by the condition monitoring system, a maintenance schedule associated with the machine based on the estimated trend in the historical particle count data.

2. The method of claim 1, further including generating an event notification if the data indicative of the current particle count deviates from the trend by the threshold amount.

3. The method of claim 2, wherein generating the event notification includes:
   generating one or more of a text message, an SMS message, an e-mail message, and an automated voice message; and
   providing the one or more generated messages to a subscriber.

4. The method of claim 1, wherein the current particle count data includes one or more of a number and size of particles present in a fluid flowing through the fluid flow channel.

5. The method of claim 1, wherein the particle detection device is disposed proximate an input port of a filtration device configured to collect and store particulate matter present in the fluid.

6. The method of claim 1, wherein the historic particle count data includes previously monitored data indicative of one or more of a number and size of particles present in a fluid flowing through the fluid flow channel.

7. The method of claim 1, wherein the fluid flow channel is associated with the hydraulic system for operating one or more hydraulically-actuated devices of the machine.

8. A system for early detection of component failure in a hydraulic system comprising:
   a particle detection device disposed in a fluid flow channel of a machine, the particle detection device configured to monitor a current particle count associated with fluid flowing through the fluid flow channel; and
   a condition monitoring system in wireless data communication with the particle detection device, the condition monitoring system configured to:
   receive data indicative of the current particle count;
   analyze historic particle count data collected by the particle detection device;
   estimate a trend in the historic particle count data based on the analysis;
   update a maintenance schedule associated with the machine based on the estimated trend in the historical particle count data; and
   predict a failure event associated with one or more components associated with the fluid flow channel if the data indicative of the current particle count deviates from the trend by a threshold amount.

9. The system of claim 8, wherein the condition monitoring system is configured to generate a failure event notification associated with a predicted failure event.

10. The system of claim 8, wherein the current particle count data includes one or more of a number and size of particles present in a fluid flowing through the fluid flow channel.

11. The system of claim 8, wherein the fluid flow channel includes a filtration device configured to collect and store particulate matter present in the fluid.

12. The system of claim 11, wherein the filtration device includes a fluid filter.

13. The system of claim 12, wherein the fluid filter includes a hydraulic fluid filter for operating an implement associated with the machine.

14. The system of claim 8, wherein the particle detection device includes a laser diode optical detector.

15. The system of claim 8, further including a data collector disposed on-board the machine, the data collector in wireless communication with the condition monitoring system and configured to:
   receive data indicative of the current particle count from the particle detection device; and
   provide data indicative of the current particle count to the condition monitoring system.

16. The system of claim 15, wherein the data collector includes an electronic control module associated with the machine.

17. The system of claim 16, wherein the condition monitoring system includes an off-board computer system.

18. The method of claim 1, further comprising predicting, by the condition monitoring system, a failure event associated with one or more components associated with the fluid flow channel if the data indicative of the current particle count deviates from the trend by a threshold amount.

19. A machine, comprising:
   a fluid flow channel for delivering fluid to one or more components associated with the machine;
   a particle detection device disposed in the fluid flow channel, the particle detection device configured to monitor a current particle count associated with fluid flowing through the fluid flow channel;

a data collector disposed on-board the machine and communicatively coupled to the particle detection device, the data collector configured to receive the particle count data from the particle detection device; and a condition monitoring system in wireless data communication with the particle detection device, the condition monitoring system configured to:

analyze historic particle count data collected by the particle detection device;

estimate a trend in the historic particle count data based on the analysis;

predict a failure event associated with the one or more components associated with the fluid flow channel if the data indicative of the current particle count deviates from the trend by a threshold amount;

update a maintenance schedule associated with the machine based on the estimated trend in the historical particle count data; and generate a failure event notification associated with a predicted failure event.

20. The machine of claim 19, wherein the particle detection device includes a laser diode optical detector.

* * * * *